United States Patent
Hauck et al.

(10) Patent No.: US 8,809,533 B2
(45) Date of Patent: Aug. 19, 2014

(54) BI- OR TRICYCLIC STERICALLY HINDERED ALKOXYAMINES AND PROCESS FOR THEIR PREPARATION

(71) Applicants: Stefan Hauck, Lampertheim (DE); Walter Fischer, Reinach (CH); Kai-Uwe Schoening, Oberwil (CH)

(72) Inventors: Stefan Hauck, Lampertheim (DE); Walter Fischer, Reinach (CH); Kai-Uwe Schoening, Oberwil (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/045,860

(22) Filed: Oct. 4, 2013

(65) Prior Publication Data

US 2014/0039100 A1 Feb. 6, 2014

Related U.S. Application Data

(63) Continuation of application No. 13/389,271, filed on Feb. 24, 2012, now Pat. No. 8,598,369.

(30) Foreign Application Priority Data

Aug. 11, 2009 (EP) .................................... 09167625

(51) Int. Cl.
*C07D 491/04* (2006.01)
*C08K 5/353* (2006.01)
*C08K 5/3435* (2006.01)
*C07D 209/52* (2006.01)
*C07D 211/94* (2006.01)

(52) U.S. Cl.
CPC ............... *C08K 5/3435* (2013.01); *C08K 5/353* (2013.01); *C07D 491/04* (2013.01); *C07D 209/52* (2013.01); *C07D 211/94* (2013.01)
USPC .......................................................... 546/89

(58) Field of Classification Search
None
See application file for complete search history.

(56) References Cited

U.S. PATENT DOCUMENTS

| | | | |
|---|---|---|---|
| 5,004,770 A | 4/1991 | Cortolano | |
| 5,096,950 A | 3/1992 | Galbo | |
| 5,204,473 A | 4/1993 | Winter et al. | |
| 7,943,809 B2 * | 5/2011 | Benage et al. | 585/5 |
| 8,524,812 B2 | 9/2013 | Sala et al. | |
| 2012/0083557 A1 | 4/2012 | Schoening | |
| 2012/0108709 A1 | 5/2012 | Schoening et al. | |

FOREIGN PATENT DOCUMENTS

WO 2004/076419 A1 9/2004

* cited by examiner

*Primary Examiner* — Heidi Reese
(74) *Attorney, Agent, or Firm* — Tyler A. Stevenson

(57) ABSTRACT

The instant invention pertains to novel bi- or tricyclic sterically hindered alkoxyamines, their precursors, a process for their preparation and their use as light stabilizers for polymers or coatings, as flame retardants, as peroxide substitutes (rheology modifiers) or carbon radical scavengers.

10 Claims, No Drawings

BI- OR TRICYCLIC STERICALLY HINDERED ALKOXYAMINES AND PROCESS FOR THEIR PREPARATION

The instant invention pertains to novel bi- or tricyclic sterically hindered alkoxyamines, a process for their preparation and their use as light stabilizers for polymers or coatings, as flame retardants, as peroxide substitutes (rheology modifiers) or carbon radical scavengers.

The preparation of 2,2,6,6-tetramethylpiperidine-based N-alkoxyamines (NOR) from the respective hindered amine light stabilizers (HALS) is a straightforward process and usually involves an oxidation step to form the corresponding N-oxyl radical and a subsequent coupling step with alkyl radicals. The NORs formed in this process usually do not contain functional groups other than esters or 1,3,5-triazine amines since most other functional groups deteriorate in these processes. However, NORs bearing functional groups are of particular interest as they could have interesting properties and devise the way towards new applications. Of particular interest are transformations which lead to a high density in terms of functionalization in low molecular weight compounds. This patent application pertains to novel NOR structures, which can be obtained by means of a simple and cost-effective reaction sequence. Surprisingly, it was found that 4-oxo-NORs can be transformed into bicyclic compounds when applying a simple three step synthesis. Thus, when preparing enamines from these substrates followed by an allylic halogenation and reaction with a nucleophile, entirely new NORs can be obtained. The compounds prepared can be used as (reactive) light stabilizers for polymers or coatings, as light stabilizers (content protectants) in home and personal care, as flame retardants, as peroxide substitutes (rheology modifiers) or carbon radicals scavengers. Furthermore, applications as fungicides, insecticides and pesticides are conceivable.

One aspect of the invention is a compound of formula (Ia) or (Ib)

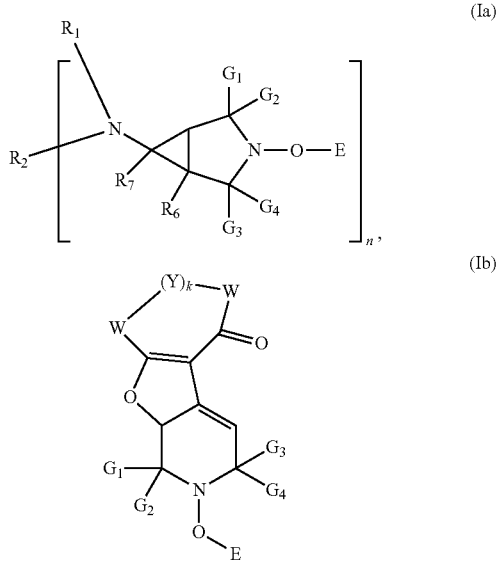

wherein $G_1$, $G_2$, $G_3$ and $G_4$ are independently alkyl of 1 to 4 carbon atoms or $G_1$ and $G_2$ and/or $G_3$ and $G_4$ are together tetramethylene or pentamethylene;

E is independently straight or branched chain $C_1$-$C_{24}$alkyl, straight or branched chain $C_2$-$C_{18}$alkenyl, $C_3$-$C_{20}$alkinyl, $C_3$-$C_{12}$cycloalkyl, $C_5$-$C_{12}$cycloalkenyl, phenyl, naphthyl or $C_7$-$C_{15}$phenylalkyl; or said straight or branched chain $C_1$-$C_{24}$ alkyl, straight or branched chain $C_2$-$C_{24}$ alkenyl, $C_3$-$C_{12}$cycloalkyl, $C_5$-$C_{12}$cycloalkenyl, $C_3$-$C_{20}$alkinyl can be substituted by one or more -halogen, —OH, —OR$_{122}$, —NH$_2$, —NHR$_{122}$, —N(R$_{122}$)$_2$, —NHCOR$_{122}$, —NR$_{122}$COR$_{122}$, —OCOR$_{122}$, —COR$_{122}$, —SO$_2$R$_{122}$, —SR$_{122}$, —SOR$_{122}$, —P(OR$_{122}$)$_3$, —P(O)(OR$_{122}$)$_2$, P(R$_{122}$)$_3$; or said straight or branched chain unsubstituted or substituted $C_1$-$C_{24}$ alkyl, straight or branched chain unsubstituted or substituted $C_2$-$C_{24}$ alkenyl, $C_5$-$C_{12}$ cycloalkyl, $C_5$-$C_{12}$cycloalkenyl or $C_2$-$C_{18}$ alkinyl can also be interrupted by one or more —O—, —NH— or —NR$_{122}$— groups or combinations thereof; or said phenyl, naphthyl or $C_7$-$C_{15}$phenylalkyl can also be substituted by one or more halogen, —CN, —CF$_3$, —NO$_2$,

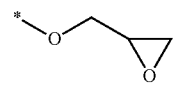

—NHR$_{122}$, —N(R$_{122}$)$_2$, —OH, —OR$_{122}$, —COR$_{122}$; wherein R$_{122}$ is hydrogen, straight or branched chain $C_1$-$C_{18}$ alkyl, straight or branched chain $C_2$-$C_{18}$ alkenyl, $C_3$-$C_{10}$ cycloalkyl, phenyl, naphthyl, or $C_7$-$C_{15}$ phenylalkyl;

W is CH$_2$ or CH$_3$;
if W is CH$_3$, k is 0
if W is CH$_2$ Y is a direct bond, CH$_2$ or C(CH$_3$)$_2$;
R$_6$ is hydrogen or halogen;
R$_7$ is hydrogen, OH, CN, halogen, $C_1$-$C_{18}$alkyl, $C_1$-$C_{18}$alkenyl, phenyl, $C_1$-$C_{18}$alkoxy, $C_1$-$C_{18}$alkylthio, NR$_{10}$R$_{11}$ wherein R$_{10}$ and R$_{11}$ are independently $C_1$-$C_{12}$ alkyl or together are $C_3$-$C_{12}$cycloalkyl, morpholine and substituted morpholine or piperazine and substituted piperazine or they form a group

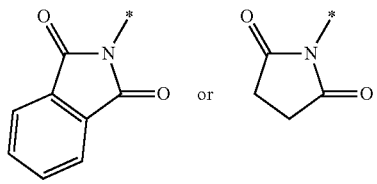 [SMILES: *N1C(=O)c2ccccc2C1=O ; *N1C(=O)CCC1=O]

wherein * is the point of attachment;
n is 1 or 2
if n is 1
R$_1$ and R$_2$ are independently straight or branched chain $C_1$-$C_{24}$alkyl, $C_5$-$C_{12}$cycloalkyl, phenyl, naphthyl or $C_7$-$C_{15}$phenylalkyl; or
R$_1$ and R$_2$ together with the nitrogen atom to which they are attached form a 5 to 7 membered ring which may contain a further nitrogen, sulfur or oxygen atom; and which may be further substituted;
if n is 2
R$_1$ is straight or branched chain $C_1$-$C_{24}$alkyl, $C_5$-$C_{12}$cycloalkyl, phenyl, naphthyl or $C_7$-$C_{15}$phenylalkyl;
R$_2$ is $C_1$-$C_{12}$alkylene, $C_1$-$C_{12}$alkenylene, $C_5$-$C_7$cycloalkylene or phenylene; or
R$_1$ and R$_2$ together with the nitrogen atom to which they are attached form a piperazin-di-yl radical which may be substituted.

Substituted 5 to 7 membered rings, in particular piperazine and morpholine rings are, for example, N-(2-hydroxyethyl) piperazine; N-(2-aminoethyl)piperazine; methylpiperazine isomers; dimethyl piperazine isomers; piperazine 2-carboxylic acid; 2-phenylpiperazine; 2,3-diphenyl piperazine; 2-biphenyl-4-yl-piperazine; 2-(naphthalen-2-yl)piperazine or 2,6-dimethylmorpholine; 2,5-dimethylpyrrolidine.

Halogen is fluorine, chlorine, bromine and iodine.

The alkyl radicals in the various substituents may be linear or branched. Examples of alkyl containing 1 to 20 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

$C_3$-$C_{12}$cycloalkyl is typically cyclopropyl, cyclopentyl, methylcyclopentyl, dimethylcyclopentyl, cyclohexyl, methylcyclohexyl.

$C_3$-$C_{20}$alkenyl is, for example, propenyl, butenyl, pentenyl, hexenyl, heptenyl, octenyl, dodecenyl including their isomers.

$C_7$-$C_{12}$phenylalkyl is for example benzyl, phenylpropyl, α,α-dimethylbenzyl or α-methyl-benzyl.

$C_3$-$C_{20}$alkynyl is preferably propargyl.

Alkyl substituted by —OH is typically 2-hydroxyethyl, 2-hydroxypropyl or 2-hydroxybutyl.

For example, E is straight or branched chain $C_1$-$C_{12}$alkyl, which alkyl may be unsubstituted or substituted by 1 OH group.

For instance $G_1$, $G_2$, $G_3$ and $G_4$ are methyl.

Preferably $R_7$, is hydrogen, OH, CN, Cl, phenyl, $C_1$-$C_{12}$alkoxy or a group

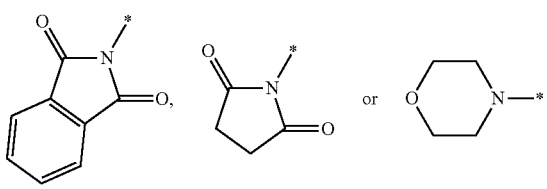 [SMILES: *N1C(=O)c2ccccc2C1=O ; *N1C(=O)CCC1=O ; *N1CCOCC1]

wherein * is the point of attachment.

The preparation of the compounds of formulae (Ia) and (Ib) starts from 4-oxo-tetramethylpiperidine which can be oxidized to the nitroxide radical and then reacted to the corresponding N—O—R compound of formula (O)

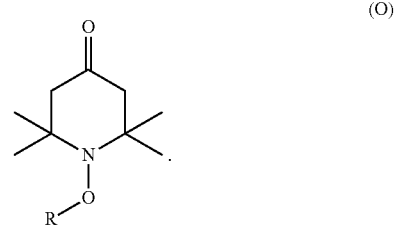

(O)

The preparation and use of N—O—R compounds is, for example, described in U.S. Pat. Nos. 5,004,770 and 5,096,950.

The following scheme explains the individual steps of the preparation procedure starting from a compound of formula (O).

Reaction Scheme I

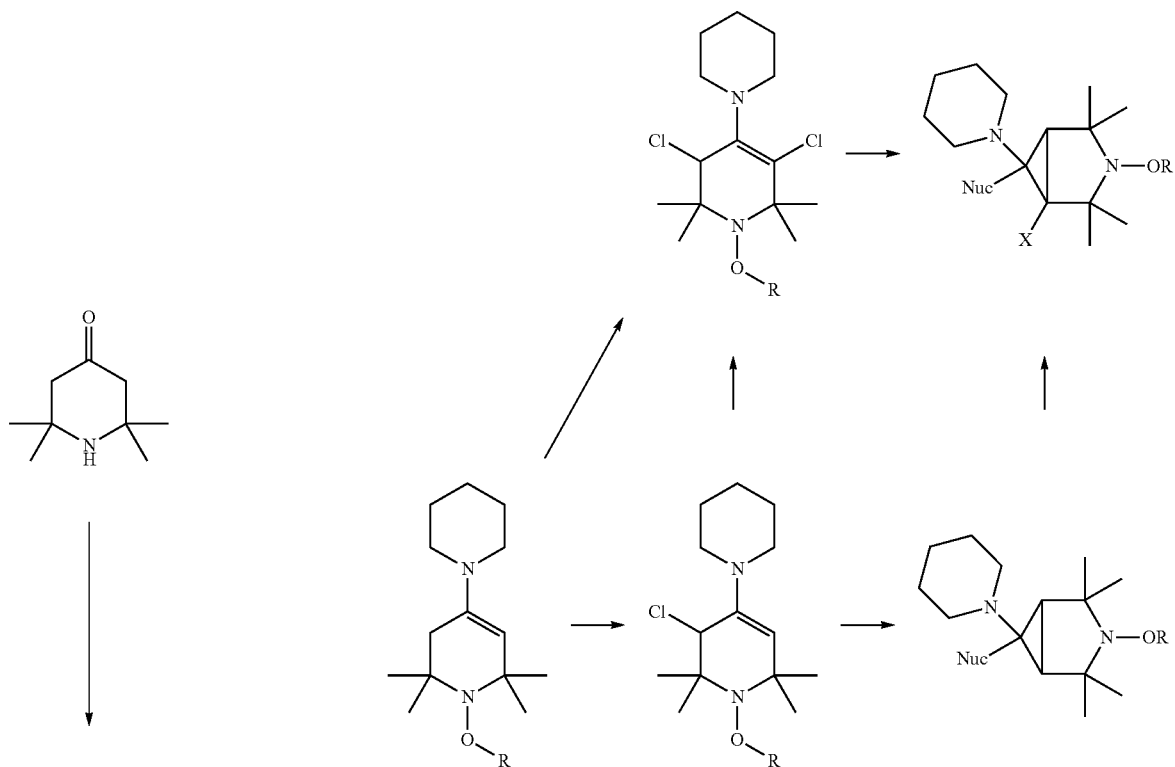

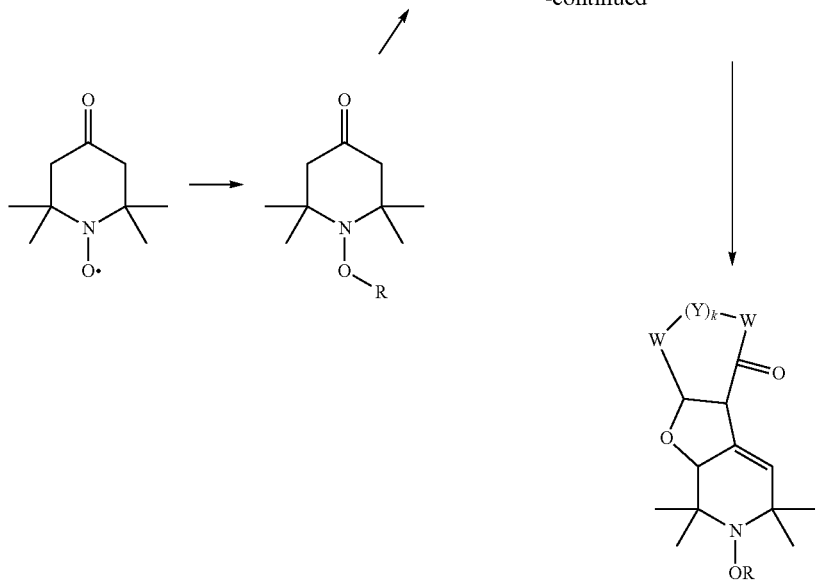

For the sake of clarity, the reaction scheme illustrates the individual reactions starting from 4-oxo tetramethylpiperidine-1-alkoxyamine which is reacted with piperidine to form a specific enamine.

In general enamines are synthesized starting from 4-oxo-NOR and an excess of the desired secondary amine. The reaction is typically carried out under Dean-Stark-conditions in a suitable solvent, such as toluene, n-heptane or n-hexane with or without p-toluene sulfonic acid as catalyst. Temperatures range from 60° C. to 140° C. Alternatively, other acid catalysts such as Dowex-50, montmorillonite K 10, and acetic acid or lewis acids, such as $TiCl_a$, $(iPrO)_4Ti$ can be used. Additionally or alternatively, dehydrating agents can be applied such as molecular sieves, sodium sulfate, calcium chloride, calcium oxide, or magnesium sulfate. The formation of enamines is known in principal and, for example, described in "Preparation of enamines"; Chem. Enamines (1994), 467-521, Wiley; Chichester; UK.

The chlorination of the enamines is carried out by dropping a solution of N-chlorosuccinimide (NCS) or dimethyl sulfide-N-chlorosuccinimide complex in a suitable solvent, for example, dichloromethane, ethylene dichloride, chloroform or carbon tetrachloride, to a solution of the enamine in the same solvent, cooled to a temperature between −78° C. and room temperature over a short period of time. For the synthesis of chloro enamines, NCS is used in a molar ratio of 1:1-1.1 in relation to the enamine. For the synthesis of double halogenated enamines, a molar ratio of 1:2.1-2.2 is used. For the preparation of differently substituted halogenated enamines, a two step synthesis is required. In each step a molar ratio of 1:1.1 between enamine and halogenating agent is used. Alternatively, other chlorinating agents can be used, such as chlorine, $SbCl_5$, sulfuryl chloride, thionyl chloride, N-chloro compounds, chloramine-T, and phosphorus chlorides.

For brominations, N-bromosuccinimide or bromine is used.

Dimethyl succinimido sulfonium fluoro sulfate or dimethyl succinimido sulfonium chloride can be used for the synthesis of sulfonium salt substituted enamines (Angew. Chem., Int. Ed. Engl. (1979), 18, 800). These compounds can be converted in analogy to the halogenated compounds.

This type of chlorination is, for example, described in J. Chem. Soc., Perkin Trans. 2 (1993); 1907.

Depending on the nucleophile to be attached, reaction conditions for the preparation of bicyclic sterically hindered alkoxyamines vary. Usually temperatures are between −30° C. and 140° C., most preferably 70-80° C. Solvents for the reaction are water, nitriles, glycoles, DMF, DMA, alcohols, THF, ethers or combinations of the solvents. Most preferably acetonitrile is used. Suitable bases for the reaction are carbonates, most preferably $Cs_2CO_3$, or organic bases, most preferably sterically hindered ones like 1,5,7-triazabicyclo[4.4.0]dec-5-ene (TBD) or diazabicyclononane (DBN). Reaction times vary between 1 hour and 3 days.

The compound of formula (Ib) can be synthesized starting from the respective chloro enamines. Both, mono chloro enamines and bis-chloro enamines are suitable for this reaction. The stoichiometry of the reaction requires a two fold excess of the 1,3-diketo compound and a 2.5 fold excess of a suitable base. Most preferably $Cs_2CO_3$ is used. Reactions are, for example, carried out in nitriles, glycoles, dimethylformamide (DMF), dimethylacetamide (DMA), alcohols, tetrahydrofurane (THF), ethers or combination of the solvents. Most preferably acetonitrile is used. Temperatures are between room temperature (RT) and 140° C. Most preferably the conversion is carried out at 70-80° C. Reaction times are within days.

The above outlined synthesis starts from the respective sterically hindered alkoxyamines. It is, however, also possible to start from the respective sterically hindered amine (NH compound) or nitroxyl (NO. compound). The oxidation step and the formation of the alkoxyamine are then the final reaction steps.

In general it is possible to combine the chlorination step and the subsequent conversion into the bicyclic structures in a one-pot-synthesis.

An aspect of the instant invention is a process for the preparation of a compound of formula Ia or Ib comprising the steps a) reacting a compound of formula (II)

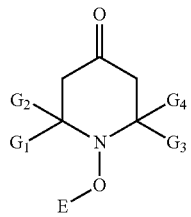
(II)

with an amino compound of formula (III)

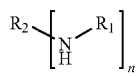
(III)

to form an enamine of formula (IV)

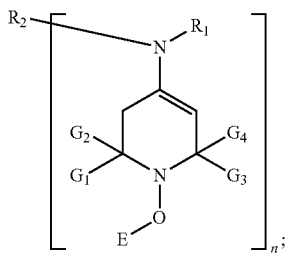
(IV)

b) halogenating a compound of formula (IV) to yield a compound of formula (Va) or (Vb)

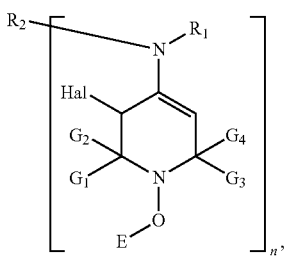
(Va)

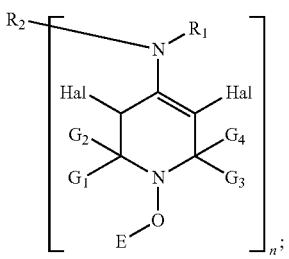
(Vb)

c) reacting a compound of formula (Va) or (Vb) with a nucleophile to yield a compound of formula (Ia)

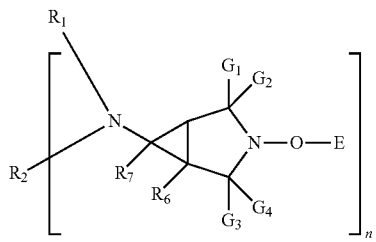
(Ia)

or d) reacting a compound of formula (Va) with a compound of formula (VI)

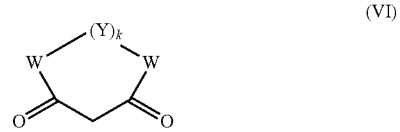
(VI)

to yield a compound of formula (Ib)

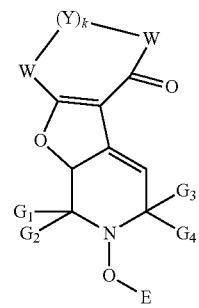
(Ib)

wherein the substituents $G_1, G_2, G_3, G_4, E, Y, W, R_1, R_2, R_6$ and $R_7$, n and k have the meaning as defined above.

Typical nucleophiles are, for example, hydride, hydroxide, cyanide, halogenides, $C_1$-$C_{18}$alkyl carbanions, $C_1$-$C_{18}$alkenyl carbanions or vinylanions, phenyl anions, $C_1$-$C_{18}$ alkoxides, $C_1$-$C_{18}$ alkylthiolates, amides of $NR_{10}R_{11}$ wherein $R_{10}$ and $R_{11}$ are independently $C_1$-$C_{12}$ alkyl or together are $C_3$-$C_{12}$cycloalkyl, amides of morpholine and piperazine or imide anions of the groups

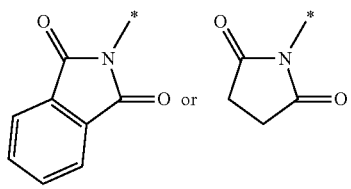

Reaction conditions and amounts have been defined above when explaining the reaction scheme I.

A further aspect of the invention is a composition which comprises
(a) an organic polymer subject to the adverse effects of heat, oxygen and light, and
(b) one or more compounds according to formula (Ia) or (Ib) as defined above.

For example component (a) is a thermoplastic organic polymer or a coating binder.

Suitable organic polymers and binders are mentioned below.

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethyllene-propylene copolymers, LDPE/ethylene-vinyl acetate copolymers (EVA), LDPE/ethyleneacrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stepreoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrilealkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethyllene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or polym-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimides, polyesterimides, polyhydantoins and polybenzimidazoles.

18. Polyesters derived from dicarboxylic acids and diols and/or from hydroxycarboxylic acids or the corresponding lactones or lactides, for example polyethylene terephthalate, polybutylene terephthalate, poly-1,4-dimethylolcyclohexane terephthalate, polyalkylene naphthalate and polyhydroxybenzoates as well as copolyether esters derived from hydroxyl-terminated polyethers, and also polyesters modified with polycarbonates or MBS. Copolyesters may comprise, for example—but are not limited to—polybutylenesuccinate/terephtalate, polybutyleneadipate/terephthalate, polytetramethyleneadipate/terephthalate, polybutylensuccinate/adipate, polybutylensuccinate/carbonate, poly-3-hydroxybutyrate/octanoate copolymer, poly-3-hydroxybutyrate/hexanoate/decanoate terpolymer. Furthermore, aliphatic polyesters may comprise, for example—but are not limited to—the class of poly(hydroxyalkanoates), in particular, poly(propiolactone), poly(butyrolactone), poly(pivalolactone), poly(valerolactone) and poly(caprolactone), polyethylenesuccinate, polypropylenesuccinate, polybutylenesuccinate, polyhexamethylenesuccinate, polyethyleneadipate, polypropyleneadipate, polybutyleneadipate, polyhexamethyleneadipate, polyethyleneoxalate, polypropyleneoxalate, polybutyleneoxalate, polyhexamethyleneoxalate, polyethylenesebacate, polypropylenesebacate, polybutylenesebacate and polylactic acid (PLA) as well as corresponding polyesters modified with polycarbonates or MBS. The term "polylactic acid (PLA)" designates a homo-polymer of preferably poly-L-lactide and any of its blends or alloys with other polymers; a co-polymer of lactic acid or lactide with other monomers, such as hydroxy-carboxylic acids, like for example glycolic acid, 3-hydroxy-butyric acid, 4-hydroxy-butyric acid, 4-hydroxy-valeric acid, 5-hydrooxy-valeric acid, 6-hydroxy-caproic acid and cyclic forms thereof; the terms "lactic acid" or "lactide" include L-lactic acid, D-lactic acid, mixtures and dimers thereof, i.e. L-lactide, D-lactide, meso-lacide and any mixtures thereof.

19. Polycarbonates and polyester carbonates.

20. Polyketones.

21. Polysulfones, polyether sulfones and polyether ketones.

22. Crosslinked polymers derived from aldehydes on the one hand and phenols, ureas and Meamines on the other hand, such as phenol/formaldehyde resins, urea/formaldehyde resins and melamine/formaldehyde resins.

23. Drying and non-drying alkyd resins.

24. Unsaturated polyester resins derived from copolyesters of saturated and unsaturated dicarboxylic acids with polyhydric alcohols and vinyl compounds as crosslinking agents, and also halogen-containing modifications thereof of low flammability.

25. Crosslinkable acrylic resins derived from substituted acrylates, for example epoxy acrylates, urethane acrylates or polyester acrylates.

26. Alkyd resins, polyester resins and acrylate resins crosslinked with melamine resins, urea resins, isocyanates, isocyanurates, polyisocyanates or epoxy resins.

27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

29. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

Particular preference is given to polyolefins and polystyrene.

In one embodiment the composition comprises a further component selected from solvents, pigments, dyes, plasticizers, antioxidants, thixotropic agents, levelling assistants, further light stabilizers, metal passivators, metal oxides, organophosphorus compounds, hydroxylamines, UV absorbers, sterically hindered amines, and mixtures thereof.

Examples for such further components are given below.
1. Antioxidants
  1.1. Alkylated monophenols
  1.2. Alkylthiomethylphenols
  1.3. Hydroquinones and alkylated hydroquinones
  1.4. Tocopherols
  1.5. Hydroxylated thiodiphenyl ethers
  1.6. Alkylidenebisphenols
  1.7. O-, N- and S-benzyl compounds
  1.8. Hydroxybenzylated malonates
  1.9. Aromatic hydroxybenzyl compounds
  1.10. Triazine compounds
  1.11. Benzylphosphonates
  1.12. Acylaminophenols
  1.13. Esters of β-(3,5-di-tert-butyl-4-hydroxyphenyl)propionic acid with mono- or polyhydric alcohols
  1.14. Esters of β-(5-tert-butyl-4-hydroxy-3-methylphenyl) propionic acid with mono- or polyhydric alcohols
  1.15. Esters of β-(3,5-dicyclohexyl-4-hydroxyphenyl)propionic acid with mono- or polyhydric alcohols
  1.16. Esters of 3,5-di-tert-butyl-4-hydroxyphenyl acetic acid with mono- or polyhydric alcohols
  1.17. Amides of β-(3,5-di-tert-butyl-4-hydroxyphenyl)propionic acid
  1.18. Ascorbic acid (vitamin C)
  1.19. Aminic antioxidants
2. UV absorbers and light stabilizers
  2.1. 2-(2'-Hydroxyphenyl)benzotriazoles
  2.2. 2-Hydroxybenzophenones
  2.3. Esters of substituted and unsubstituted benzoic acids
  2.4. Acrylates
  2.5. Nickel compounds
  2.6. Other sterically hindered amines
  2.7. Oxamides
  2.8. 2-(2-Hydroxyphenyl)-1,3,5-triazines
3. Metal deactivators
4. Phosphites and phosphonites
5. Hydroxylamines
6. Nitrones
7. Thiosynergists
8. Peroxide scavengers
9. Polyamide stabilizers
10. Basic co-stabilizers
11. Nucleating agents
12. Fillers and reinforcing agents
13. Other additives, for example plasticisers, lubricants, emulsifiers, pigments, rheology additives, catalysts, flow-control agents, optical brighteners, flameproofing agents, antistatic agents and blowing agents.
14. Benzofuranones and indolinones Examples from each of the above groups are described in further detail in U.S. Pat. No. 6,878,761.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized compositions of the invention may optionally also contain from about 0.01 to about 5%, preferably from about 0.025 to about 2%, and especially from about 0.1 to about 1% by weight, based on the weight of the polymer of various conventional additives, such as the materials listed above, or mixtures thereof.

Yet further aspects of the invention are a process for stabilizing an organic polymeric material against damage by light, oxygen and/or heat, which comprises adding to or applying to said material at least one compound according to formula (Ia) or (Ib) as described above and the use of a compound according to formula (Ia) or (Ib) as described above for stabilizing an organic polymer against damage by light, oxygen and/or heat or as flame retardant.

The compounds of formula (IV), (Va) and (Vb) are intermediates for the compounds of formula (Ia) and (Ib), however they are themselves also useful as stabilizers for polymers and, therefore, also an aspect of the invention.

Also subject of the invention is a compound of formula (IV)

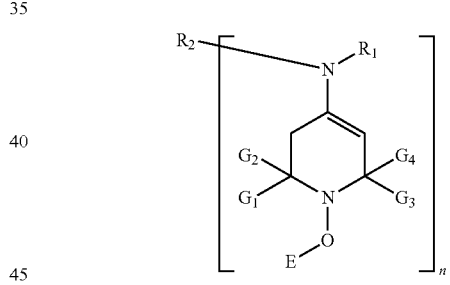

wherein $G_1$, $G_2$, $G_3$ and $G_4$ are independently alkyl of 1 to 4 carbon atoms or $G_1$ and $G_2$ and/or $G_3$ and $G_4$ are together tetramethylene or pentamethylene;

E is independently hydrogen, straight or branched chain $C_1$-$C_{24}$alkyl, straight or branched chain $C_2$-$C_{18}$alkenyl, $C_2$-$C_{18}$alkinyl, $C_5$-$C_{12}$cycloalkyl, $C_5$-$C_{12}$cycloalkenyl, phenyl, naphthyl or $C_7$-$C_{15}$phenylalkyl; or said straight or branched chain $C_1$-$C_{24}$ alkyl, straight or branched chain $C_2$-$C_{24}$ alkenyl, $C_5$-$C_{12}$cycloalkyl, $C_5$-$C_{12}$cycloalkenyl, $C_2$-$C_{18}$alkinyl can be substituted by one or more -halogen, —OH, —OR$_{122}$, —NH$_2$, —NHR$_{122}$, —N(R$_{122}$)$_2$, —NHCOR$_{122}$, —NR$_{122}$COR$_{122}$, —OCOR$_{122}$, —COR$_{122}$, —SO$_2$R$_{122}$, —SR$_{122}$, —SOR$_{122}$, —P(OR$_{122}$)$_3$, —P(O)(OR$_{122}$)$_2$, P(R$_{122}$)$_3$; or said straight or branched chain unsubstituted or substituted $C_1$-$C_{24}$ alkyl, straight or branched chain unsubstituted or substituted $C_2$-$C_{24}$ alkenyl, $C_5$-$C_{12}$ cycloalkyl, $C_5$-$C_{12}$cycloalkenyl or $C_2$-$C_{18}$ alkinyl can also be interrupted by one or more —O—, —NH— or —NR$_{122}$—
groups or combinations thereof; or said phenyl, naphthyl or C$_7$-C$_{15}$phenylalkyl can also be substituted by one or more halogen, —CN, —CF$_3$, —NO$_2$,

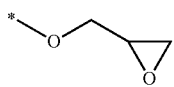

—NHR$_{122}$, —N(R$_{122}$)$_2$, —OH, —OR$_{122}$, —COR$_{122}$;
wherein

R$_{122}$ is hydrogen, straight or branched chain C$_1$-C$_{18}$ alkyl, straight or branched chain C$_2$-C$_{18}$ alkenyl, C$_5$-C$_{10}$ cycloalkyl, phenyl, naphthyl, or C$_7$-C$_{15}$ phenylalkyl;

n is 1 or 2 if n is 1

R$_1$ and R$_2$ are independently hydrogen, straight or branched chain C$_1$-C$_{24}$alkyl, straight or branched chain C$_2$-C$_{18}$alkenyl, C$_2$-C$_{18}$alkinyl, C$_5$-C$_{12}$cycloalkyl, C$_5$-C$_{12}$cycloalkenyl, phenyl, naphthyl or C$_7$-C$_{15}$-phenylalkyl; or R$_1$ and R$_2$ together with the nitrogen atom to which they are attached form a 5 to 7 membered ring which may contain a further nitrogen or oxygen atom;

if n is 2

R$_1$ is hydrogen, straight or branched chain C$_1$-C$_{24}$alkyl, straight or branched chain C$_2$-C$_{18}$alkenyl, C$_2$-C$_{18}$alkinyl, C$_5$-C$_{12}$cycloalkyl, C$_5$-C$_{12}$cycloalkenyl, phenyl, naphthyl or C$_7$-C$_{15}$phenylalkyl;

R$_2$ is C$_1$-C$_{12}$alkylene, C$_1$-C$_{12}$alkenylene, C$_5$-C$_7$cycloalkylene or phenylene; or R$_1$ and R$_2$ together with the nitrogen atom to which they are attached form a piperazin-di-yl radical;

and a compound of formula (Va) or (Vb)

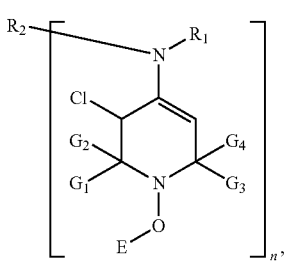

(Va)

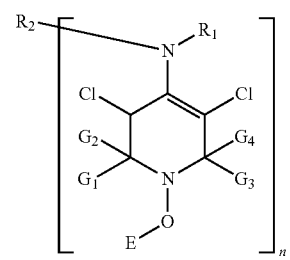

(Vb)

wherein the substituents are as defined above.

Definitions and preferences given above apply equally for all aspects of the invention.

The following examples illustrate the invention.

Preparation Examples

A) Enamines

Example 1

Procedure for the Synthesis of Compound 2

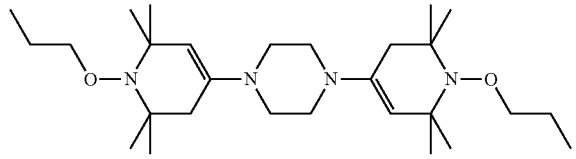 [SMILES: CCCON1C(C)(C)C=C(N2CCN(C3=CC(C)(C)N(OCCC)C(C)(C)C3)CC2)CC1(C)C]

50 g (0.234 mol) 4-oxo-NOR and 10.1 g (0.117 mol) piperazine are dissolved in 300 ml toluene and heated to reflux for 6 h. Water is removed by a Dean-Stark-apparatus. After removal of the solvent a brown oil is obtained. Treatment of the oil with methanol precipitates white crystals which are washed with methanol and dried under reduced pressure. 36.11 g (0.076 mol; 65%) of the piperazine bis enamine are obtained as pure white crystals.

[M+H$^+$]=477.

$^1$H NMR (300 MHz, CDCl$_3$): δ=4.35 (s, 2H); 3.76 (t, J=7.0 Hz, 4H); 2.77 (m, 8H); 2.32 (AB system, 2H); 1.85 (AB system, 2H); 1.57 (m, 4H); 1.24 (s, 18H); 1.14 (s, 6H); 0.95 (t, J=7.0 Hz, 6H)

Example 2

Procedure for the Synthesis of 5

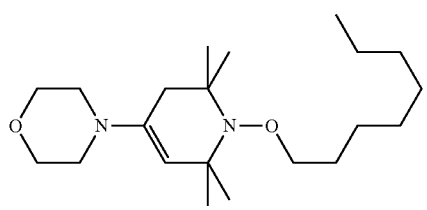 [SMILES: CCCCCCCCON1C(C)(C)C=C(N2CCOCC2)CC1(C)C]

6.6 g (21.65 mmol) 4-oxo-NOR and 1.9 g (21.65 mmol) morpholine are dissolved in 40 ml toluene. 0.08 g (0.43 mmol) p-toluene sulfonic acid monohydrate are added and the mixture is heated to reflux for 48 h. Water is removed by a Dean-Stark-apparatus. After completion of the reaction, the mixture is cooled to room temperature and washed with 50 ml water. The organic phase is separated, dried with Na$_2$SO$_4$, filtered and the solvent removed in vacuo. 6.79 g (19.27 mmol; 89%) NOR-enamine are obtained as yellow viscous oil.

[M+H$^+$]=353.

$^1$H NMR (300 MHz, CDCl$_3$): δ=4.36 (s, 1H); 3.76 (m, 6H); 2.75 (m, 4H); 2.31 (AB system, 1H); 1.86 (AB system, 1H); 1.55 (m, 2H); 1.42-1.20 (multiple m & s, 19 H); 1.15 (br s, 3H); 0.90 (t, J=7.0 Hz, 3H)

$^{13}$C NMR (75 MHz, CDCl$_3$): δ=140.0; 109.6; 77.1; 66.8; 59.9; 58.5; 53.3; 48.5; 41.6; 33.5; 31.8; 30.6; 29.6; 29.2; 28.8; 24.1; 26.5; 22.6; 21.1; 14.1

TABLE 1

| Enamine | M [g/mol] | Yield [%] | MS-Peak [M + H⁺] | Compound No. |
|---|---|---|---|---|
| (structure) | 420.64 | 58 | 421 | 1 |
| (structure) | 476.75 | 65 | 477 | 2 |
| (structure) | 254.38 | 86 | 255 | 3 |
| (structure) | 282.43 | 88 | 283 | 4 |
| (structure) | 252.57 | 89 | 353 | 5 |
| (structure) | 252.40 | 90 | 253 | 6 |
| (structure) | 238.38 | 85 | 239 | 7 |

Further Examples:

B) Halogenated Enamines

Example 3

Procedure for the Synthesis of Compound 13

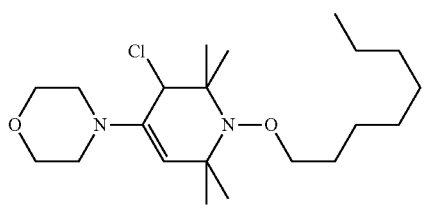 [SMILES: CCCCCCCCON1C(C)(C)C=C(N2CCOCC2)C(Cl)C1(C)C]

4 g (10.21 mmol) 4-morpholino-NOR are dissolved in 20 ml dichloromethane and cooled under protective gas atmosphere to −70° C. Then 1.4 g (10.21 mmol) N-chlorosuccinimide, dissolved in 80 ml dichloromethane are added drop wise over a period of 1 h. The mixture is warmed to −30° C. and stirred for additional 4 h. Then, the reaction mixture is washed with 30 ml saturated $Na_2CO_3$-solution and 100 ml water. The organic layers are separated, dried with $Na_2SO_4$, filtered and the solvent is removed in vacuo. 3.5 g (9.04 mmol; 89%) of the morpholino-chloroenamine NOR are obtained as yellow oil.

[M+H$^+$]=387

$^1$H NMR (300 MHz, CDCl$_3$): δ=4.37 (s, 1H); 4.00 (s, 1H); 3.74 (m, 2H); 3.68 (m, 4H); 2.78 (m, 4H); 1.46 (m, 2H); 1.37-1.10 (multiple m+s, 22H); 0.81 (t, J=7.0 Hz, 3H)

Example 4

Procedure for the Synthesis of Compound 16

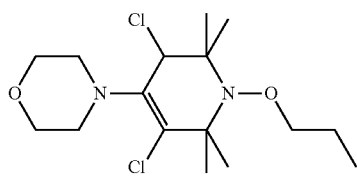 [SMILES: CCCON1C(C)(C)C(Cl)=C(N2CCOCC2)C(Cl)C1(C)C]

2.13 g (6.72 mmol) 4-morpholino-NOR are dissolved in 20 ml dichloromethane and cooled under protective gas atmosphere to −70° C. Then 0.898 g (6.72 mmol) N-chlorosuccinimide, dissolved in 30 ml dichloromethane are added drop wise over a period of 1 h. The mixture is warmed to −30° C. and stirred for additional 4 h. The reaction mixture is then washed with 30 ml saturated $Na_2CO_3$-solution and 100 ml water. The organic layers are separated, dried with $Na_2SO_4$, filtered and the solvent is removed in vacuo. 2.0 g (5.69 mmol; 85%) of the morpholino-bischloroenamine NOR are obtained as light yellow oil.

[M+H$^+$]=351

$^1$H NMR (400 MHz, CDCl$_3$): δ=4.23 (s, 1H); 3.72 (m, 2H); 3.68 (m, 4H); 3.06 (m, 2H); 2.78 (m, 2H); 1.50 (m, 2H); 1.35 (s, 3H); 1.32 (s, 6H); 1.12 (s, 3H); 0.87 (t, J=7.5 Hz, 3H)

$^{13}$C NMR (100 MHz, CDCl$_3$): δ=137.9; 129.4; 79.0; 67.3; 65.1; 64.4; 62.0; 49.7; 30.9; 27.5; 21.9; 21.3; 20.6; 10.9

Example 5

Procedure for the Synthesis of Compound 9

2.4 g (5.03 mmol) piperazine bis enamine are dissolved in 70 ml dichloromethane and cooled to −70° C. under protective gas atmosphere. Then 1.3 g (10.06) N-chlorosuccinimide dissolved in 30 ml dichloromethane are added drop wise over a period of 1 h. The mixture is warmed to −30° C. and stirred for additional 2 h. Then, the reaction mixture is washed with 30 ml saturated $Na_2CO_3$-solution and 100 ml water. The organic layers are separated, dried with $Na_2SO_4$, filtered and the solvent is removed in vacuo. 2.7 g (4.98 mmol) bis chloro bis enamine NOR are obtained as pure white powder.

[M+H$^+$]=546

$^1$H NMR (300 MHz, CDCl$_3$): δ=4.48 (s, 2H); 4.11 (s, 2H); 3.80 (t, J=6.6 Hz, 4H); 2.94 (ps, 8H); 1.58 (m, 4H); 1.42 (s, 6H); 1.32 (s, 6H); 1.25 (s, 6H); 1.21 (2, 6H); 0.96 (t, J=7.3 Hz, 6H)

TABLE 2

Further Examples

| Chloro enamine | M [g/mol] | Yield [%] | MS-Peak [M + H$^+$] | Compound No. |
|---|---|---|---|---|
|  | 489.53 | 98 | 489 | 8 |

TABLE 2-continued

Further Examples

| Chloro enamine | M [g/mol] | Yield [%] | MS-Peak [M + H⁺] | Compound No. |
|---|---|---|---|---|
| (structure) | 545.64 | 99 | 545 | 9 |
| (structure) | 288.82 | 63 | 289 | 10 |
| (structure) | 316.87 | 44 | 317 | 11 |
| (structure) | 361.33 | 20 | 362 | 12 |
| (structure) | 387.01 | 89 | 387 | 13 |
| (structure) | 286.85 | 20 | 287 | 14 |
| (structure) | 272.82 | 55 | 273 | 15 |
| (structure) | 351.32 | 85 | 351 | 16 |

TABLE 2-continued

Further Examples

| Chloro enamine | M [g/mol] | Yield [%] | MS-Peak [M + H⁺] | Compound No. |
|---|---|---|---|---|
| | 421.46 | 47 | 421 | 17 |

C) Bicyclic Sterically Hindered Alkoxyamines

Example 7

Procedure for the Synthesis of Compound 18

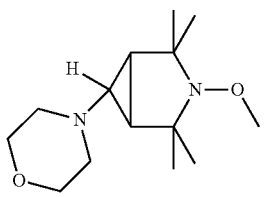 [SMILES: CON1C(C)(C)C2C(N3CCOCC3)C2C1(C)C]

0.2 g (0.69 mmol) morpholino chloroenamine NOR are dissolved in 20 ml acetonitrile. 0.26 g (6.92 mmol) NaBH$_4$ are added. The mixture is stirred at 50° C. for 4 d. Then the mixture is treated with 10 ml water and extracted with 50 ml dichloromethane. The organic layer is separated, dried with Na$_2$SO$_4$, filtered and the solvent is removed in vacuo. 0.171 g (0.67 mmol; 97%) of a colourless oil are obtained, which solidifies at room temperature to give a white powder.

[M+H⁺]=255

$^1$H NMR (400 MHz, CDCl$_3$): δ=3.71 (m, 4H); 3.59 (s, 3H); 2.59 (m, 4H); 1.52 (t, J=7.3 Hz, 1H); 1.28 (s, 6H); 1.24 (s, 6H); 1.17 (d, J=7.3 Hz, 2H)

$^{13}$C NMR (100 MHz, CDCl$_3$): δ=66.8; 64.8; 63.7; 56.1; 51.3; 29.3; 28.1; 24.8

Example 8

Procedure for the Synthesis of Compound 19

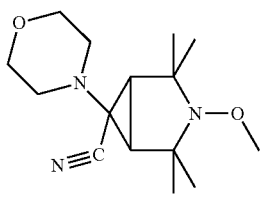 [SMILES: CON1C(C)(C)C2C(C1(C)C)C2(C#N)N1CCOCC1]

1.8 g (6.312 mmol) morpholino chloroenamine NOR are dissolved in 20 ml acetonitrile. 0.4 g (1.262 mmol) hexadecyl trimethyl ammonium chloride and 0.45 g (9.468 mmol) NaCN, dissolved in 2 ml water, are added. The mixture is heated to 70° C. for 3 h. Then the mixture is cooled to room temperature, washed with 10 ml saturated Na$_2$CO$_3$-solution and extracted with 20 ml ethylacetate. The combined organic phases are washed with 40 ml water, separated, dried with Na$_2$SO$_4$ and filtered. After removal of the solvent in vacuo, 1.7 g (6.08 mmol; 97%) of a light yellow powder are obtained.

[M+H⁺]=280

$^1$H NMR (300 MHz, CDCl$_3$): δ=3.75 (br s, 4H); 3.57 (s, 3H); 2.79 (br s, 4H); 1.80 (s, 2H); 1.31 (s, 6H); 1.29 (s, 6H)

$^{13}$C NMR (100 MHz, CDCl$_3$): δ=117.8; 66.4; 64.9; 64.4; 53.5; 47.2; 37.4; 27.5; 24.2

Example 9

Procedure for the Synthesis of Compound 36

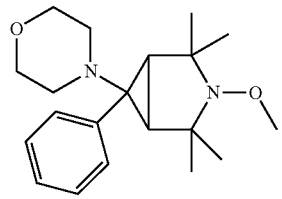 [SMILES: CON1C(C)(C)C2C(C1(C)C)C2(c1ccccc1)N1CCOCC1]

0.2 g (0.692 mmol) morpholino chloroenamine NOR are dissolved in 20 ml diethyl ether under protective gas atmosphere and cooled to −50° C. Then 1.1 ml of a 1.9 M phenyl-lithium solution in dibutyl ether are added drop wise over 30 minutes. The mixture is warmed to room temperature over night and the reaction mixture is quenched by adding 20 ml water. The organic layers are separated, washed with 20 ml saturated Na$_2$CO$_3$-solution, 10 ml water and dried with Na$_2$SO$_4$. The solution is concentrated to 5 ml and chromatographed on silica gel with 2:1 hexane/ethylacetate to give 0.069 g (0.207 mmol; 30%) product as a white solid.

[M+H⁺]=331

$^1$H NMR (400 MHz, CDCl$_3$): δ=7.29 (m, 2H); 7.21 (m, 1H); 7.14 (m, 2H); 3.68 (m, 4H); 3.64 (s, 3H); 2.92 (m, 2H); 2.11 (m, 2H); 1.57 (s, 2H); 1.52 (s, 3H); 1.44 (br s, 9H)

$^{13}$C NMR (100 MHz, CDCl$_3$): δ=134.8; 130.3; 128.2; 127.5; 67.0; 64.9; 64.2; 53.2; 37.7; 29.7

Example 10

Procedure for the Synthesis of Compound 37 Starting from Compound 24

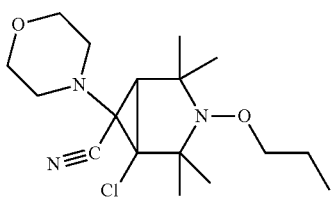 [SMILES: CCCON1C(C)(C)C2C(C#N)(N3CCOCC3)C2(Cl)C1(C)C]

0.500 g (1.63 mmol) 24 are dissolved in 70 ml dichloromethane and cooled to −70° C. under protective gas atmosphere. Then 0.238 g (1.78 mmol) N-chlorosuccinimide dissolved in 30 ml dichloromethane are added drop wise over a period of 1 h. The mixture is warmed to −30° C. and stirred for additional 2 h. Then, the reaction mixture is washed with 30 ml saturated $Na_2CO_3$-solution and 100 ml water. The organic layers are separated, dried with $Na_2SO_4$, filtered and the solvent is removed in vacuo. 0.474 g (1.38 mmol; 85%) 37 are obtained as white powder.

$[M+H^+]=342$ $^1$H NMR (400 MHz, $CDCl_3$): δ=3.77 (m, 2H); 3.61 (m, 4H); 2.74 (m, 4H); 1.56 (s, 1H); 1.48 (m, 2H); 1.36 (s, 3H); 1.28 (s, 3H); 1.26 (s, 3H); 1.21 (s, 3H); 0.88 (t, J=7.5 Hz, 3H)

$^{13}$C NMR (100 MHz, $CDCl_3$): δ=114.8; 78.8; 66.6; 66.3; 64.3; 55.0; 53.4; 49.7; 46.3; 27.4; 24.2; 24.9; 23.6; 22.2; 11.0

TABLE 3

Further Examples

| Structure | M [g/mol] | Yield [%] | MS-Peak [M + H$^+$] | Compound No. |
|---|---|---|---|---|
| 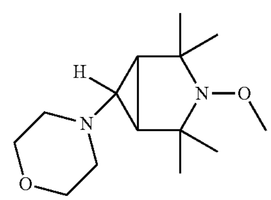 [SMILES: CON1C(C)(C)C2C(N3CCOCC3)C2C1(C)C] | 254.38 | 97 | 255 | 18 |
| 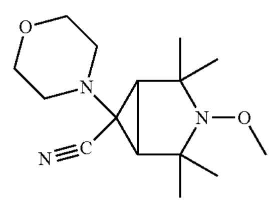 [SMILES: CON1C(C)(C)C2C(C1(C)C)C2(C#N)N1CCOCC1] | 279.39 | 97 | 280 | 19 |
| 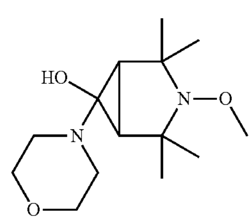 [SMILES: CON1C(C)(C)C2C(C1(C)C)C2(O)N1CCOCC1] | 270.37 | 70 | 271 | 20 |
| 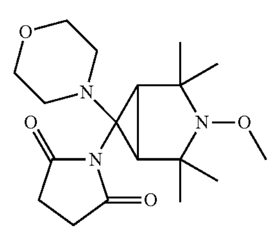 [SMILES: CON1C(C)(C)C2C(C1(C)C)C2(N1CCOCC1)N1C(=O)CCC1=O] | 351.45 | 83 | 352 | 21 |

TABLE 3-continued
| Further Examples | | | | |
|---|---|---|---|---|
| Structure | M [g/mol] | Yield [%] | MS-Peak [M + H+] | Compound No. |
| 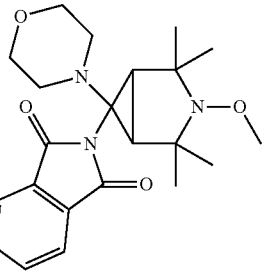 | 399.49 | 27 | 400 | 22 |
| 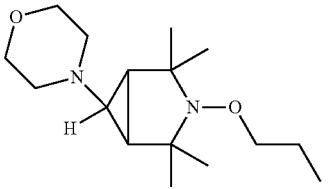 [SMILES: CCCON1C(C)(C)C2C(N3CCOCC3)C2C1(C)C] | 282.43 | 88 | 283 | 23 |
| 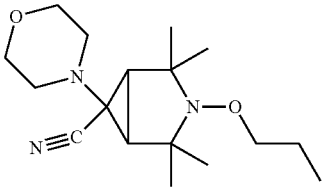 [SMILES: CCCON1C(C)(C)C2C(C1(C)C)C2(C#N)N1CCOCC1] | 307.44 | 88 | 308 | 24 |
| 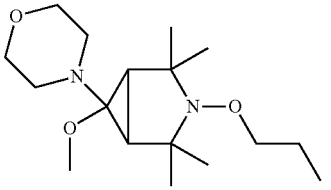 [SMILES: CCCON1C(C)(C)C2C(C1(C)C)C2(OC)N1CCOCC1] | 312.46 | 65 | 313 | 25 |
| 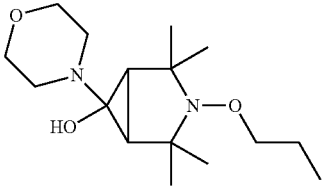 [SMILES: CCCON1C(C)(C)C2C(C1(C)C)C2(O)N1CCOCC1] | 298.43 | 74 | 299 | 26 |
| 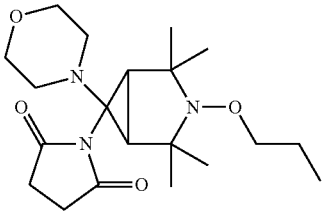 [SMILES: CCCON1C(C)(C)C2C(C1(C)C)C2(N1CCOCC1)N1C(=O)CCC1=O] | 379.50 | 57 | 380 | 27 |

TABLE 3-continued

Further Examples

| Structure | M [g/mol] | Yield [%] | MS-Peak [M + H+] | Compound No. |
|---|---|---|---|---|
| 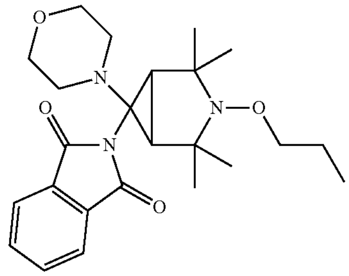 [SMILES: CCCON1C(C)(C)C2C(C1(C)C)C2(N1CCOCC1)N1C(=O)c2ccccc2C1=O] | 427.55 | 27 | 428 | 28 |
| 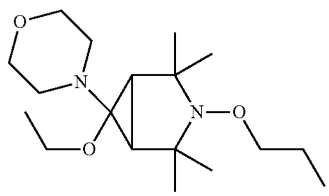 [SMILES: CCCON1C(C)(C)C2C(C1(C)C)C2(OCC)N1CCOCC1] | 326.48 | 68 | 327 | 29 |
| 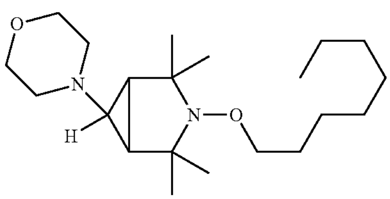 [SMILES: CCCCCCCCON1C(C)(C)C2C(N3CCOCC3)C2C1(C)C] | 352.57 | 88 | 353 | 30 |
| 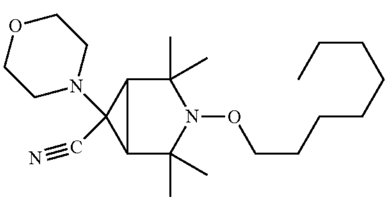 [SMILES: CCCCCCCCON1C(C)(C)C2C(C1(C)C)C2(C#N)N1CCOCC1] | 377.58 | 77 | 378 | 31 |
| 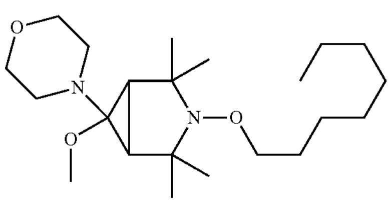 [SMILES: CCCCCCCCON1C(C)(C)C2C(C1(C)C)C2(OC)N1CCOCC1] | 382.59 | 86 | 383 | 32 |
| 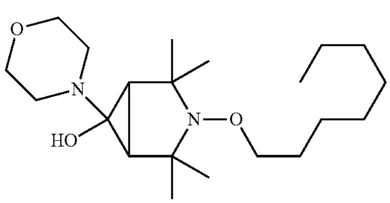 | 368.56 | 84 | 369 | 33 |
| 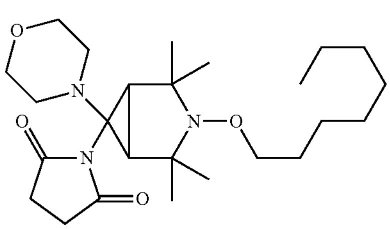 [SMILES: CCCCCCCCON1C(C)(C)C2C(C1(C)C)C2(N1CCOCC1)N1C(=O)CCC1=O] | 449.64 | 52 | 450 | 34 |

TABLE 3-continued

Further Examples

| Structure | M [g/mol] | Yield [%] | MS-Peak [M + H⁺] | Compound No. |
|---|---|---|---|---|
| 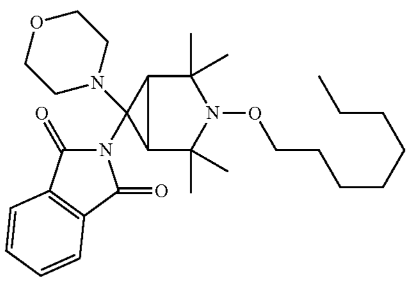 [SMILES: CCCCCCCCON1C(C)(C)C2C(C1(C)C)C2(N1CCOCC1)N1C(=O)c2ccccc2C1=O] | 497.68 | 58 | 498 | 35 |
| 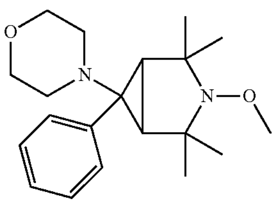 [SMILES: CON1C(C)(C)C2C(C1(C)C)C2(c1ccccc1)N1CCOCC1] | 330.47 | 30 | 331 | 36 |
| 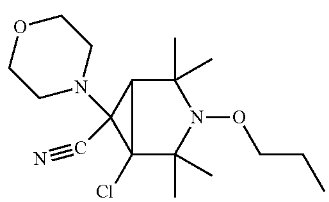 [SMILES: CCCON1C(C)(C)C2C(C#N)(N3CCOCC3)C2(Cl)C1(C)C] | 341.88 | 85 | 342 | 37 |
| 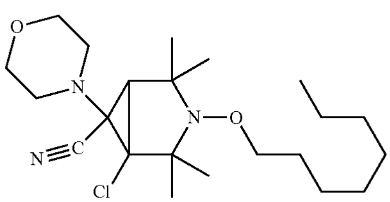 [SMILES: CCCCCCCCON1C(C)(C)C2C(C#N)(N3CCOCC3)C2(Cl)C1(C)C] | 412.02 | 75 | 412 | 38 |

Example 11

Procedure for the Synthesis of Compound 42

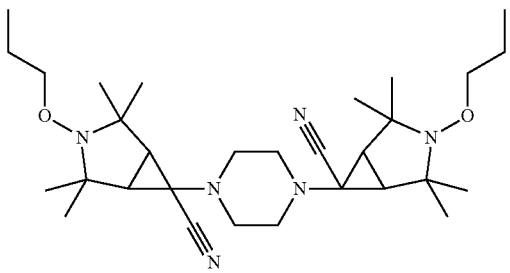 [SMILES: CCCON1C(C)(C)C2C(C1(C)C)C2(C#N)N1CCN(C2(C#N)C3C2C(C)(C)N(OCCC)C3(C)C)CC1]

0.54 g (0.99 mmol) piperazine bis chloro enamine NOR are dissolved in a mixture of 20 ml acetonitrile and 10 ml 1,2-dichloroethane. A solution of 0.098 g (2.00 mmol) NaCN in 2 ml water and 0.046 g (0.2 mmol) hexadecyl trimethyl ammonium chloride are added. The mixture is heated to 70° C. for 24 h. After cooling to room temperature, the reaction mixture is washed with 30 ml water and extracted with 30 ml dichloromethane. The organic layers are dried with Na$_2$SO$_4$, filtered and the solvent is evaporated in vacuo. 0.430 g (0.82 mmol; 82%) are obtained as pure white powder.

[M+H⁺]=527

$^1$H NMR (300 MHz, CDCl$_3$): δ=3.62 (t, J=6.6 Hz, 4H); 2.92 (m, 4H); 2.56 (m, 2H); 1.72 (s, 4H); 1.47 (m, 4H); 1.23 (br s, 24H); 0.87 (t, J=7.5 Hz, 6H)

TABLE 4

Further Examples

| Structure | M [g/mol] | Yield [%] | MS-Peak [M + H+] | Compound No. |
|---|---|---|---|---|
| 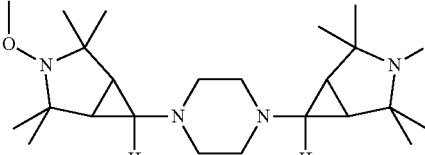 | 420.64 | 70 | 421 | 39 |
| 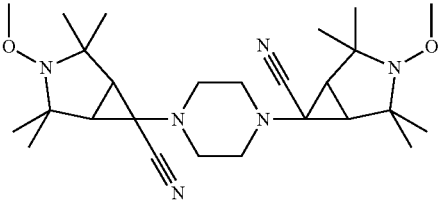 [SMILES: CON1C(C)(C)C2C(C1(C)C)C2(C#N)N1CCN(C2(C#N)C3C2C(C)(C)N(OC)C3(C)C)CC1] | 470.66 | 68 | 471 | 40 |
| 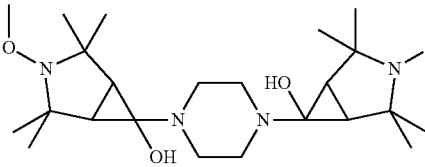 | 452.64 | 50 | 453 | 41 |
| 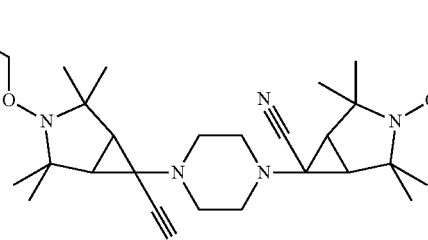 | 526.77 | 82 | 527 | 42 |
| 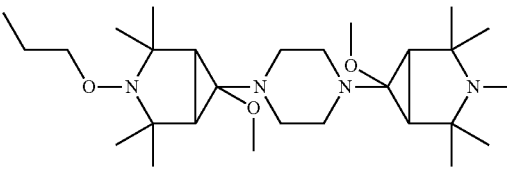 | 536.81 | 56 | 537 | 43 |

Condensed Bi- or Tricyclic NORs

Example 12

Procedure for the Synthesis of Compound 46

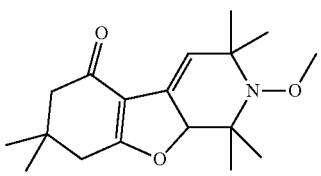

0.2 g (0.692 mmol) of morpholino chloro enamine and 0.146 g (1.039 mmol) dimedone are dissolved in 20 ml acetonitrile. 0.215 g (1.731 mmol) 1,5-Diazabicyclo[4.3.0]non-5-ene are added and the mixture was heated to reflux for 2 days. The mixture is then washed with 50 ml water. The organic layers are separated, dried with Na$_2$SO$_4$ and filtered over silica gel. After removal of the solvent in vacuo, 0.19 g (0.62 mmol; 90%) product are obtained as light yellow viscous oil.

[M+H$^+$]=306

$^1$H NMR (400 MHz, CDCl$_3$): δ=5.79 (s, 1H); 4.85 (s, 1H); 3.67 (s, 3H); 2.45 (AB system, 1H); 2.31 (AB system, 2H); 2.22 (AB system, 1H); 1.43 (s, 3H); 1.30 (s, 3H); 1.23 (s, 3H); 1.14 (s, 6H); 1.07 (s, 6H); 0.95 (s, 3H)

$^{13}$C NMR (100 MHz, CDCl$_3$): δ=193.4; 181.4; 128.1; 121.9; 113.4; 91.1; 66.1; 61.3; 61.0; 51.5; 38.4; 34.2; 31.7; 28.9; 28.3; 26.1; 23.7; 14.8

IR(neat): ν=2962; 2932; 2879; 1717; 1677; 1652; 1595; 1429; 1357; 1221; 1143; 1046 [cm$^{-1}$]

Alternative Procedure for the Synthesis of Compound 46

0.4 g (0.817 mmol) of compound 8 of example 8 and 0.268 g (2.043 mmol) dimedone are dissolved in 20 ml acetonitrile.

0.304 g (2.451 mmol) 1,5-Diazabicyclo[4.3.0]non-5-ene are added and the mixture is heated to reflux for 1 day. The mixture is then washed with 50 ml brine. After extraction with 90 ml ethyl acetate, organic layers are separated, dried with Na$_2$SO$_4$ and filtered over silica gel. 0.430 g (1.408 mmol; 86%) of the product are obtained as light yellow viscous oil.

TABLE 5

Further Examples

| Structure | M (g/mol) | Yield (%) | MS-Peak [M + H$^+$] | Compound No. |
|---|---|---|---|---|
| 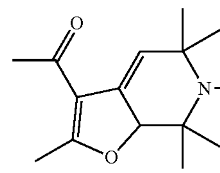 | 265.36 | 49 | 266 | 44 |
| 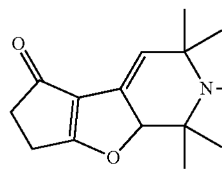 | 263.34 | 8 | 264 | 45 |
| 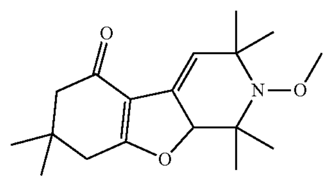 | 305.42 | 90 | 306 | 46 |
| 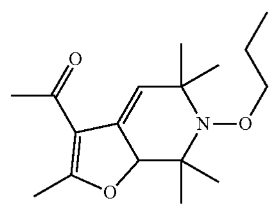 [SMILES: CCCON1C(C)(C)C=C2C(C(C)=O)=C(C)OC2C1(C)C] | 293.41 | 52 | 294 | 47 |
| 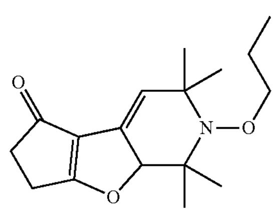 [SMILES: CCCON1C(C)(C)C=C2C3=C(CCC3=O)OC2C1(C)C] | 291.39 | 11 | 292 | 48 |
| 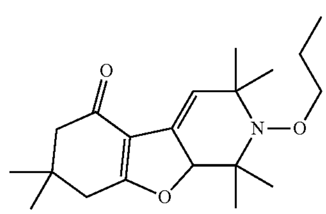 [SMILES: CCCON1C(C)(C)C=C2C3=C(CC(C)(C)CC3=O)OC2C1(C)C] | 333.47 | 97 | 334 | 49 |
| 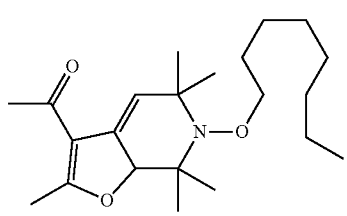 [SMILES: CCCCCCCCON1C(C)(C)C=C2C(C(C)=O)=C(C)OC2C1(C)C] | 363.55 | 53 | 364 | 50 |

TABLE 5-continued

Further Examples

| Structure | M (g/mol) | Yield (%) | MS-Peak [M + H⁺] | Compound No. |
|---|---|---|---|---|
| 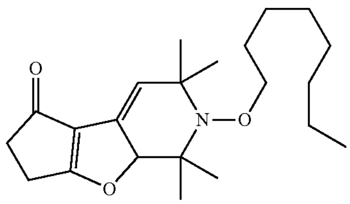 [SMILES: CCCCCCCCON1C(C)(C)C=C2C3=C(CCC3=O)OC2C1(C)C] | 361.53 | 31 | 362 | 51 |
| 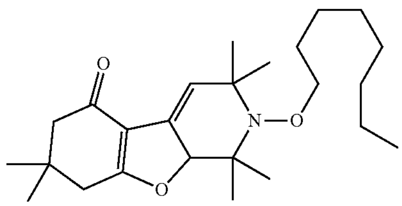 [SMILES: CCCCCCCCON1C(C)(C)C=C2C3=C(CC(C)(C)CC3=O)OC2C1(C)C] | 403.61 | 71 | 404 | 52 |

Example 13

Illustrates a "One Pot" Synthesis 1.27 g (5.00 mmol) of compound 3 are dissolved in 30 ml dichloromethane under protective gas atmosphere and cooled to −70° C. Then a solution of 0.734 g (5.5 mmol) N-chlorosuccinimide in 30 ml dichlormethane is added. The mixture is stirred for 2 h and then warmed to room temperature. After an additional hour of stirring, the solvent is removed in vacuo and 0.38 g (7.75 mmol) NaCN are added. The mixture is dissolved in 50 ml of a 1:10 mixture of water/acetonitrile and heated to 79° C. for 3 h. Then the mixture is cooled to room temperature, washed with 10 ml saturated $Na_2CO_3$-solution and extracted with 20 ml ethylacetate. The combined organic phases are washed with 40 ml water, separated, dried with $Na_2SO_4$ and filtered. After removal of the solvent in vacuo, 1.14 g (4.1 mmol; 82%) of compound 19 are obtained as a white powder. For compound 19: [M+H⁺]=280.

Application Examples

1. Stabilization of Polyols

The stabilization of polyols is tested by measuring the auto-oxidation temperatures via differential scanning calorimetry
Conditions:
Polyol: Lupranol 2084 (Elastogran)
Temperature range: 40° C.-400° C.
Ramp rate: 5° C./min
Heating conditions: under air
Anti-scorch system loading: 0.45% (referred to polyol)
Results for auto-oxidation temperatures: Unstabilized polyol: 140° C.
Stabilized sample with 19: 177° C.
Stabilized sample with 49: 176° C.
Compounds 19 and 49 are tested 2. Test as Flame Retardant in PP Films Compounds 18 and 40 are tested as flame retardant additives in PP films. Polypropylene (Moplen® HF500 N) is extruded on a co-rotating twin-screw extruder ZSK18 (Coperion Werner & Pfleiderer) at a temperature of $T_{max}$=190° C. (heating zones 1-7), a throughput rate of 1 kg/h and 100 rpm with the addition of a basic-level stabilization (0.3% IRGANOX B225+0.05% Ca-stearate, IRGANOX B225 is a 1:1 mixture of IRGAFOS 168 and IRGANOX 1010) and 0.5 weight % of each of the compounds 18 and 40. After cooling in a water bath, the polymer strand is granulated. Test specimens are prepared by compression moulding (films 250×110 mm, thickness=0.2 mm, Fontune TP200, 230° C.). Test films are tested under DIN 4102-1 B2 test conditions and compared to Flamestab NOR 116 (commercial product of Ciba Specialty Chemicals) as reference.

TABLE A

| Compound | Burning time [s] | Damaged length [mm] |
|---|---|---|
| Blank PP (no additives) | 46.3 | 190 |
| Flamestab NOR 116 | 26.1 | 99 |
| Compound of example 18 | 13.6 | 95 |
| Compound of example 40 | 15.6 | 87 |

DIN 4102-B2 (Edge Ignition, Flame length 40 mm, Distance 16 mm). PP Film Thickness 200 microns; Length: 190 mm; Width: 90 mm; Conditioning Procedure: 3 days 50%/23° C. in conditioning chamber; Lab. humidity 50%/Temp: 23° C.

3. Test as Light Stabilizer in Home & Personal Care Products

The stabilizing effect of compound 46 in a cosmetic formulation containing a dye is tested. 1% of compound 46 is pre-dissolved in Emulgin (PEG-40 Hydrogenated Castor Oil) before addition to the following surfactant-based test formulation.

| Compound | Conc. [%] |
|---|---|
| Texapon NSO | 30 |
| Dehyton K | 10 |
| PURICOLOR Blue ABL9 (FD&C Blue No. 1) | 0.001 |
| Citric Acid | to pH 5 |
| Water | to 100 |

Light Stability Testing:

The samples are irradiated in a SUNTEST XLS+Xenon lamp:
Light Intensity: 500 W/m²
Sample Chamber Temperature: 30-32° C.

Adjustment of Irradiation Spectrum: Indoor conditions (behind a window)
Used Bottles: 30 ml borax glass bottles Pictures are taken during irradiation to document the shade changes. Compound 46 stabilizes the formulation for 14 h, whereas the unstabilized sample discolors after 7 hours irradiation.

4. Light Stabilization of Polypropylene

A polypropylene basis formulation consisting of PP EE 013 AE (78.4% weight %; Borealis), carbon black master batch FK Schwarz 34-270/TPO (1.5%), talk powder Luzenac A-20 (20.0%; Luzenac), Irganox B 215 FF (0.05%; Ciba/BASF), and Ca-stearate (0.05%) is compounded in a twin-screw extruder (25 mm) at 220° C. and subsequently granulated. 50 g of this compound and 50 mg each of the additives of the examples 18 and 40 are kneaded in a brabender under nitrogen at 200° C. for 10 min. The resulting melt is pressed at 230° C. to yield plaques of 1 mm thickness. Test specimens (20*60 mm) are produced and exposed to light-induced ageing according to Fakra (lightfastness under high temperature conditions, DIN 75202), PSA and SAEJ 2412 (accelerated exposure of automotive interior components using a controlled irradiance xenon-arc apparatus) conditions. To determine the light stabilization efficiency of the parent compounds, the gloss of the sample specimens is measured at an angle of 85° and the color difference delta E upon light exposure. The data in table 2 indicate the time of failure, i.e. the period after which a delta E>2 and a gloss reduction of 50% of the starting value was measured.

TABLE B

| | Compound of example 18 - time to failure in h | Compound of example 40 - time to failure in h |
|---|---|---|
| PSA (50% of initial gloss) | >2500 | 2500 |
| PSA dE > 2 | 1500 | 1500 |
| Fakra (50% of initial gloss) | >2500 | >2500 |
| Fakra dE > 2 | 2500 | 2500 |
| SAE J (50% of initial gloss) | >3000 | >3000 |
| SAE J dE > 2 | 3000 | 3000 |

The invention claimed is:

1. A compound of formula (Ib)

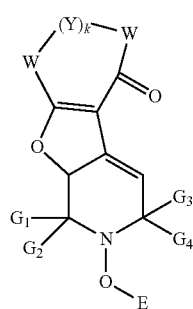

wherein
$G_1$, $G_2$, $G_3$ and $G_4$ are independently alkyl of 1 to 4 carbon atoms or $G_1$ and $G_2$ and/or $G_3$ and $G_4$ are together tetramethylene or pentamethylene;

E is independently straight or branched chain $C_1$-$C_{24}$alkyl, straight or branched chain $C_2$-$C_{18}$alkenyl, $C_3$-$C_{20}$alkinyl, $C_3$-$C_{12}$cycloalkyl, $C_5$-$C_{12}$cycloalkenyl, phenyl, naphthyl or $C_7$-$C_{15}$phenylalkyl; where said straight or branched chain $C_1$-$C_{24}$alkyl, straight or branched chain $C_2$-$C_{24}$alkenyl, $C_3$-$C_{12}$cycloalkyl, $C_5$-$C_{12}$cycloalkenyl or $C_3$-$C_{20}$alkinyl can be substituted by one or more -halogen, —OH, —OR$_{122}$, —NH$_2$, —NHR$_{122}$, —N(R$_{122}$)$_2$, —NHCOR$_{122}$, —NR$_{122}$COR$_{122}$, —OCOR$_{122}$, —COR$_{122}$, —SO$_2$R$_{122}$, —SR$_{122}$, —SOR$_{122}$, —P(OR$_{122}$)$_3$, —P(O)(OR$_{122}$)$_2$ or P(R$_{122}$)$_3$; where said straight or branched chain unsubstituted or substituted $C_1$-$C_{24}$alkyl, straight or branched chain unsubstituted or substituted $C_2$-$C_{24}$alkenyl, $C_5$-$C_{12}$cycloalkyl, $C_5$-$C_{12}$cycloalkenyl or $C_2$-$C_{18}$alkinyl can also be interrupted by one or more —O—, —NH— or —NR$_{122}$— groups or combinations thereof; and where said phenyl, naphthyl or $C_7$-$C_{15}$phenylalkyl can also be substituted by one or more halogen, —CN, —CF$_3$, —NO$_2$,

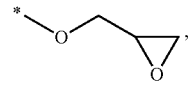

—NHR$_{122}$, —N(R$_{122}$)$_2$, —OH, —OR$_{122}$ or —COR$_{122}$; wherein R$_{122}$ is hydrogen, straight or branched chain $C_1$-$C_{18}$alkyl, straight or branched chain $C_2$-$C_{18}$ alkenyl, $C_3$-$C_{10}$cycloalkyl, phenyl, naphthyl or $C_7$-$C_{15}$phenylalkyl; and W is CH$_2$ or CH$_3$;

if W is CH$_3$, k is 0; and if W is CH$_2$, Y is a direct bond, CH$_2$ or C(CH$_3$)$_2$.

2. A compound according to claim 1 wherein E is straight or branched chain $C_1$-$C_{12}$alkyl, which alkyl may be unsubstituted or substituted by 1 OH group.

3. A compound according to claim 1 wherein $G_1$, $G_2$, $G_3$ and $G_4$ are methyl.

4. A process for the preparation of a compound of formula (Ib), which process comprises
a) reacting a compound of formula (II)

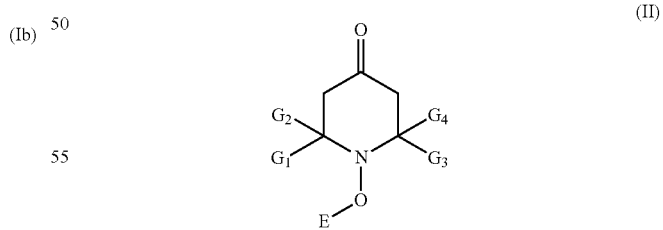

with an amino compound of formula (III)

to form an enamine of formula (IV);

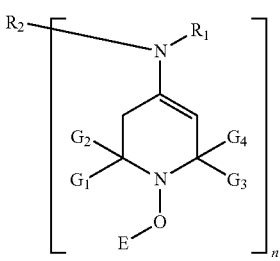

b) halogenating a compound of formula (IV) to yield a compound of formula (Va)

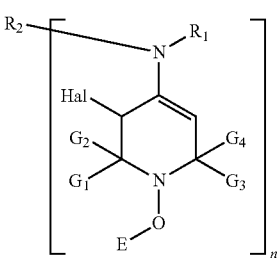

and d) reacting a compound of formula (Va) with a compound of formula (VI)

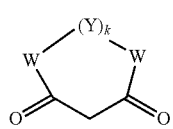

to yield a compound of formula (Ib)

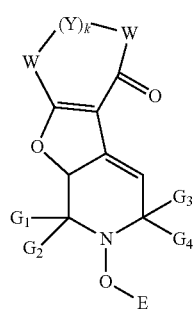

wherein
Hal is halogen;
$G_1$, $G_2$, $G_3$ and $G_4$ are independently alkyl of 1 to 4 carbon atoms or $G_1$ and $G_2$ and/or $G_3$ and $G_4$ are together tetramethylene or pentamethylene;
E is independently straight or branched chain $C_1$-$C_{24}$alkyl, straight or branched chain $C_2$-$C_{18}$alkenyl, $C_3$-$C_{20}$alkinyl, $C_3$-$C_{12}$cycloalkyl, $C_5$-$C_{12}$cycloalkenyl, phenyl, naphthyl or $C_7$-$C_{15}$phenylalkyl; where said straight or branched chain $C_1$-$C_{24}$alkyl, straight or branched chain $C_2$-$C_{24}$alkenyl, $C_3$-$C_{12}$cycloalkyl, $C_5$-$C_{12}$cycloalkenyl or $C_3$-$C_{20}$alkinyl can be substituted by one or more -halogen, —OH, —OR$_{122}$, —NH$_2$, —NHR$_{122}$, —N(R$_{122}$)$_2$, —NHCOR$_{122}$, —NR$_{122}$COR$_{122}$, —OCOR$_{122}$, —COR$_{122}$, —SO$_2$R$_{122}$, —SR$_{122}$, —SOR$_{122}$, —P(OR$_{122}$)$_3$, —P(O)(OR$_{122}$)$_2$ or P(R$_{122}$)$_3$; where said straight or branched chain unsubstituted or substituted $C_1$-$C_{24}$alkyl, straight or branched chain unsubstituted or substituted $C_2$-$C_{24}$alkenyl, $C_5$-$C_{12}$cycloalkyl, $C_5$-$C_{12}$cycloalkenyl or $C_2$-$C_{18}$alkinyl can also be interrupted by one or more —O—, —NH— or —NR$_{122}$— groups or combinations thereof; and where said phenyl, naphthyl or $C_7$-$C_{15}$phenylalkyl can also be substituted by one or more halogen, —CN, —CF$_3$, —NO$_2$,

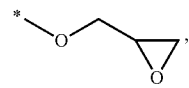

—NHR$_{122}$, —N(R$_{122}$)$_2$, —OH, —OR$_{122}$ or —COR$_{122}$; wherein R$_{122}$ is hydrogen, straight or branched chain $C_1$-$C_{18}$alkyl, straight or branched chain $C_2$-$C_{18}$alkenyl, $C_3$-$C_{10}$cycloalkyl, phenyl, naphthyl or $C_7$-$C_{15}$ phenylalkyl; and W is CH$_2$ or CH$_3$;

if W is CH$_3$, k is 0; and if W is CH$_2$, Y is a direct bond, CH$_2$ or C(CH$_3$)$_2$.

5. A composition which comprises
(a) a thermoplastic organic polymer or a coating binder and
(b) one or more compounds of formula (Ib) according to claim 1.

6. A composition according to claim 5 comprising a further component selected from solvents, pigments, dyes, plasticizers, antioxidants, thixotropic agents, levelling assistants, further light stabilizers, metal passivators, metal oxides, organophosphorus compounds, hydroxylamines, UV absorbers, sterically hindered amines and mixtures thereof.

7. A process for stabilizing an organic polymeric material against damage by light, oxygen and/or heat, which process comprises adding to or applying to said material at least one compound of formula (Ib) according to claim 1.

8. A compound of formula (IV), (Va) or (Vb)

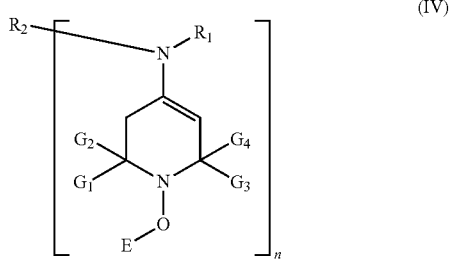

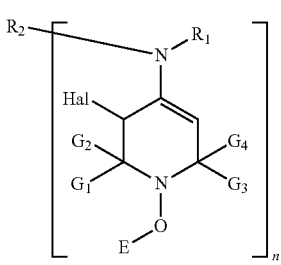

(Va)

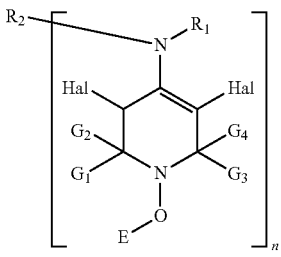

(Vb)

wherein $G_1$, $G_2$, $G_3$ and $G_4$ are independently alkyl of 1 to 4 carbon atoms or $G_1$ and $G_2$ and/or $G_3$ and $G_4$ are together tetramethylene or pentamethylene;

E is independently hydrogen, straight or branched chain $C_1$-$C_{24}$alkyl, straight or branched chain $C_2$-$C_{18}$alkenyl, $C_2$-$C_{18}$alkinyl, $C_5$-$C_{12}$cycloalkyl, $C_5$-$C_{12}$cycloalkenyl, phenyl, naphthyl or $C_7$-$C_{15}$phenylalkyl; where said straight or branched chain $C_1$-$C_{24}$alkyl, straight or branched chain $C_2$-$C_{24}$alkenyl, $C_5$-$C_{12}$cycloalkyl, $C_5$-$C_{12}$cycloalkenyl or $C_2$-$C_{18}$alkinyl can be substituted by one or more -halogen, —OH, —OR$_{122}$, —NH$_2$, —NHR$_{122}$, —N(R$_{122}$)$_2$, —NHCOR$_{122}$, —NR$_{122}$COR$_{122}$, —OCOR$_{122}$, —COR$_{122}$, —SO$_2$R$_{122}$, —SR$_{122}$, —SOR$_{122}$, —P(OR$_{122}$)$_3$, —P(O)(OR$_{122}$)$_2$ or P(R$_{122}$)$_3$; where said straight or branched chain unsubstituted or substituted $C_1$-$C_{24}$alkyl, straight or branched chain unsubstituted or substituted $C_2$-$C_{24}$alkenyl, $C_5$-$C_{12}$cycloalkyl, $C_5$-$C_{12}$cycloalkenyl or $C_2$-$C_{18}$alkinyl can also be interrupted by one or more —O—, —NH— or —NR$_{122}$— groups or combinations thereof; and where said phenyl, naphthyl or $C_7$-$C_{15}$phenylalkyl can also be substituted by one or more halogen, —CN, —CF$_3$, —NO$_2$,

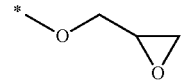

—NHR$_{122}$, —N(R$_{122}$)$_2$, —OH, —OR$_{122}$ or —COR$_{122}$; wherein R$_{122}$ is hydrogen, straight or branched chain $C_1$-$C_{18}$alkyl, straight or branched chain $C_2$-$C_{18}$alkenyl, $C_5$-$C_{10}$cycloalkyl, phenyl, naphthyl or $C_7$-$C_{15}$phenylalkyl;

n is 1 or 2;

if n is 1, $R_1$ and $R_2$ are independently hydrogen, straight or branched chain $C_1$-$C_{24}$alkyl, straight or branched chain $C_2$-$C_{18}$alkenyl, $C_2$-$C_{18}$alkinyl, $C_5$-$C_{12}$cycloalkyl, $C_5$-$C_{12}$cycloalkenyl, phenyl, naphthyl or $C_7$-$C_{15}$phenylalkyl; or $R_1$ and $R_2$ together with the nitrogen atom to which they are attached form a 5 to 7 membered ring which may contain a further nitrogen or oxygen atom;

and if n is 2, $R_1$ is hydrogen, straight or branched chain $C_1$-$C_{24}$alkyl, straight or branched chain $C_2$-$C_{18}$alkenyl, $C_2$-$C_{18}$alkinyl, $C_5$-$C_{12}$cycloalkyl, $C_5$-$C_{12}$cycloalkenyl, phenyl, naphthyl or $C_7$-$C_{15}$phenylalkyl;

$R_2$ is $C_1$-$C_{12}$alkylene, $C_1$-$C_{12}$alkenylene, $C_5$-$C_7$cycloalkylene or phenylene; or $R_1$ and $R_2$ together with the nitrogen atom to which they are attached form a piperazin-di-yl radical and Hal is halogen.

9. A composition according to claim 5 which comprises (a) a polyolefin or a polystyrene.

10. A composition according to claim 5 which comprises (a) polypropylene.

\* \* \* \* \*